(12) United States Patent
Namii et al.

(10) Patent No.: US 10,564,406 B2
(45) Date of Patent: Feb. 18, 2020

(54) OBJECTIVE OPTICAL SYSTEM FOR ENDOSCOPE

(71) Applicant: OLYMPUS CORPORATION, Hachioji-shi, Tokyo (JP)

(72) Inventors: Yasushi Namii, Hachioji (JP); Tsutomu Sasamoto, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 89 days.

(21) Appl. No.: 15/950,393

(22) Filed: Apr. 11, 2018

(65) Prior Publication Data

US 2018/0231749 A1 Aug. 16, 2018

Related U.S. Application Data

(63) Continuation of application No. PCT/JP2016/080246, filed on Oct. 12, 2016.

(30) Foreign Application Priority Data

Oct. 16, 2015 (JP) ................. 2015-204693

(51) Int. Cl.
*G02B 13/18* (2006.01)
*G02B 13/04* (2006.01)
*G02B 9/62* (2006.01)

(52) U.S. Cl.
CPC ............. *G02B 13/18* (2013.01); *G02B 13/04* (2013.01); *G02B 9/62* (2013.01)

(58) Field of Classification Search
CPC ............ G02B 13/18; G02B 13/04; G02B 9/62
(Continued)

(56) References Cited

U.S. PATENT DOCUMENTS 5,625,495 A 4/1997 Moskovich
5,999,337 A 12/1999 Ozaki
(Continued)

FOREIGN PATENT DOCUMENTS

JP 04055807 A 2/1992
JP 08166537 A 6/1996
(Continued)

OTHER PUBLICATIONS

International Search Report (ISR) dated Dec. 13, 2016 issued in International Application No. PCT/JP2016/080246.
(Continued)

*Primary Examiner* — William Choi
(74) *Attorney, Agent, or Firm* — Holtz, Holtz & Volek PC

(57) ABSTRACT

An objective optical system for endoscope includes a first group having a negative refractive power, an aperture stop, and a second group having a positive refractive power. The first group includes a negative meniscus lens having a convex surface directed toward the object side, and a positive lens having a convex surface directed toward the object side. The second group includes a predetermined lens, a positive cemented lens, and a positive single lens, or includes the predetermined lens, the positive single lens, and a positive cemented lens. The predetermined lens is a meniscus lens having a convex surface directed toward an image side. and an image-side lens, and the following conditional expressions (1'), (2), and (4') are satisfied:

$0.7 < |R1/R2| < 1.1$      (1'), $0.6 < |R1/FL| < 3$      (2), and $5 \leq |Fc/FL| \leq 7$      (4').

3 Claims, 18 Drawing Sheets

(58) Field of Classification Search
USPC ........ 359/656, 658, 659, 713, 714, 756, 763
See application file for complete search history.

(56) References Cited

U.S. PATENT DOCUMENTS

| | | | | |
|---|---|---|---|---|
| 7,466,490 | B2* | 12/2008 | Igarashi | ............. G02B 23/2438 |
| | | | | 359/645 |
| 2008/0180809 | A1 | 7/2008 | Igarashi | |
| 2013/0057666 | A1 | 3/2013 | Fujii | |

FOREIGN PATENT DOCUMENTS

| | | |
|---|---|---|
| JP | 10148754 A | 6/1998 |
| JP | 11500834 A | 1/1999 |
| JP | 11125767 A | 5/1999 |
| JP | 2008107391 A | 5/2008 |
| JP | 2009300797 A | 12/2009 |
| WO | 2011152099 A1 | 12/2011 |

OTHER PUBLICATIONS

Written Opinion dated Dec. 13, 2016 issued in International Application No. PCT/JP2016/080246.
International Preliminary Report on Patentability (IPRP) (and English language translation thereof) dated Apr. 26, 2018 issued in counterpart International Application No. PCT/JP2016/080246.
Chinese Office Action dated Nov. 4, 2019 (and English translation thereof) issued in Chinese Application No. 201680060652.1.

\* cited by examiner

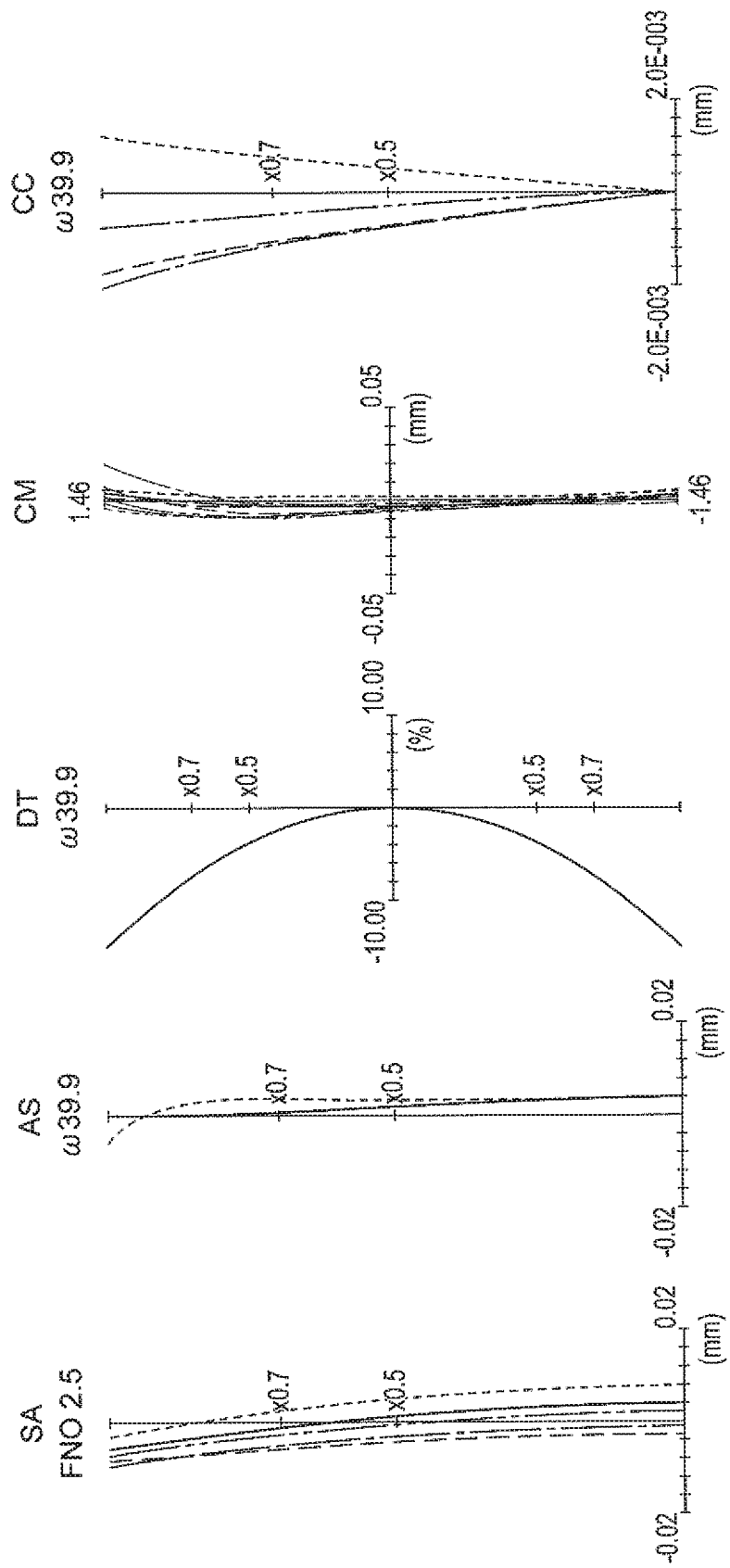

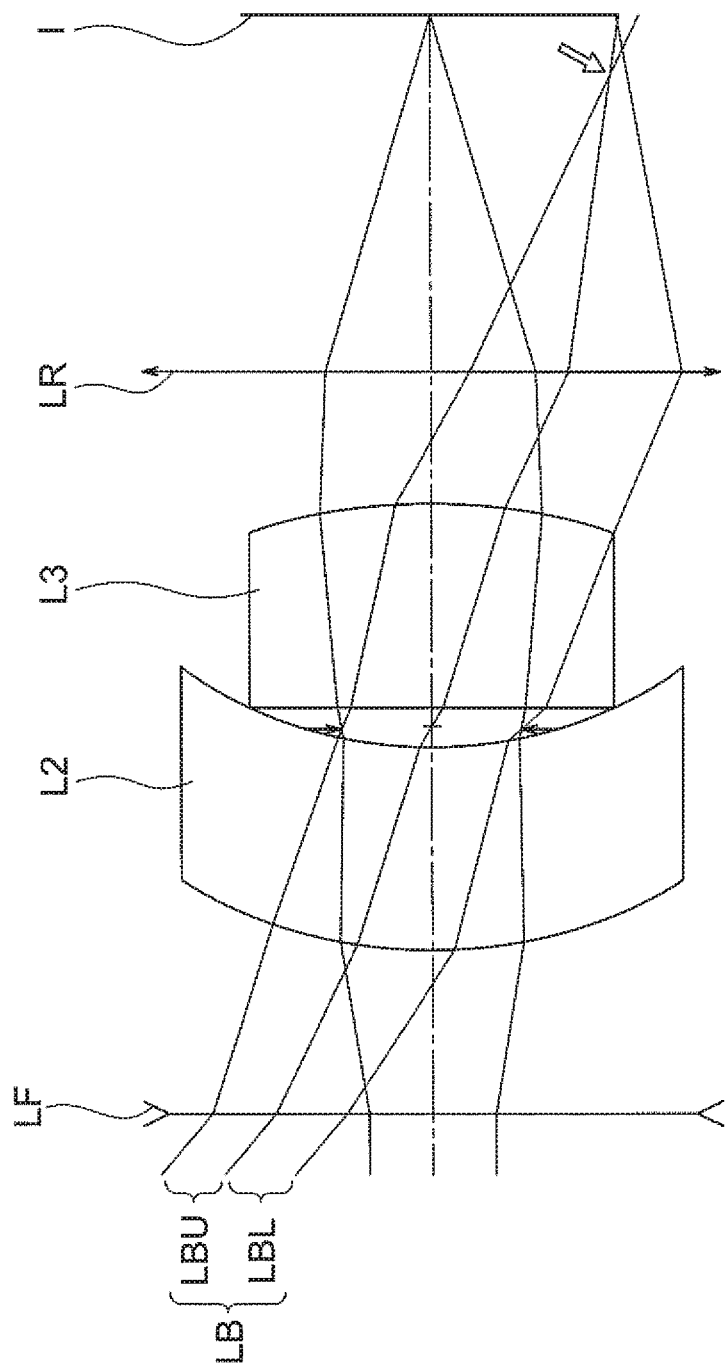

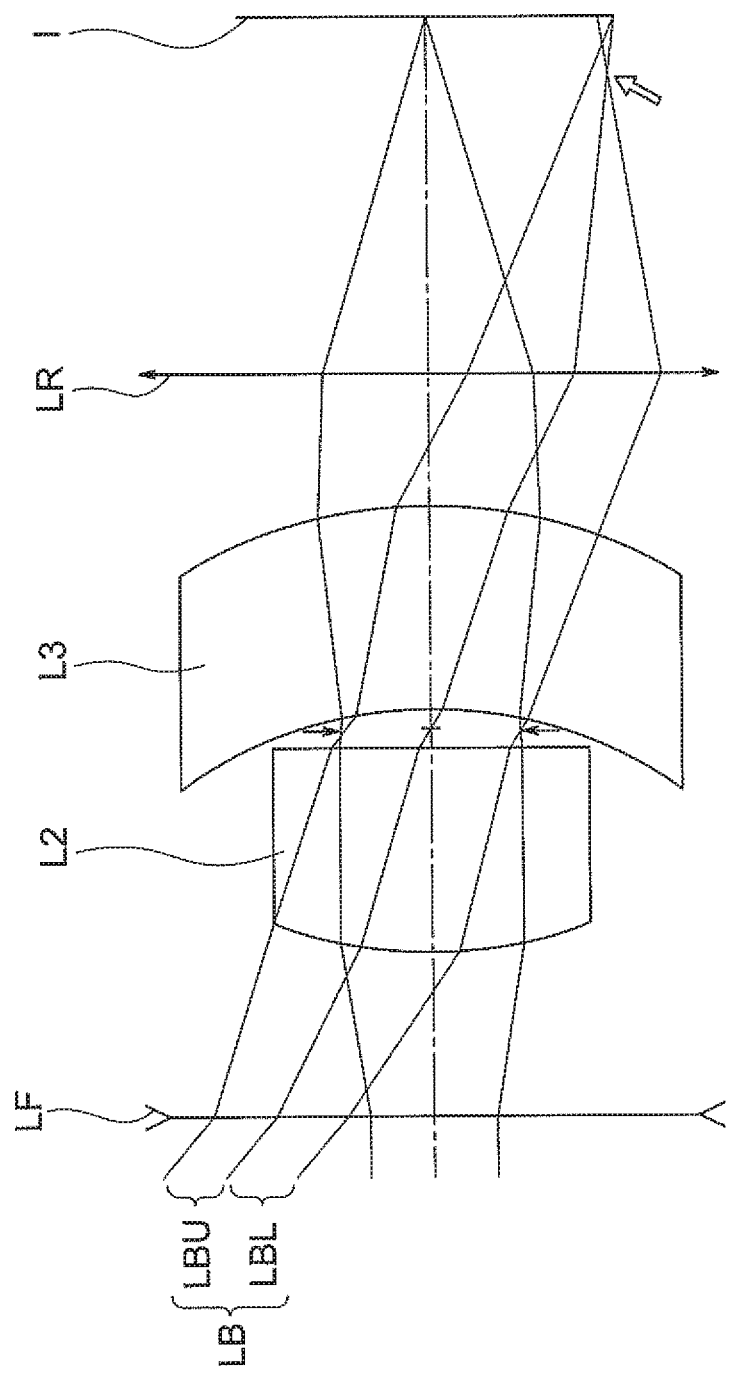

OBJECTIVE OPTICAL SYSTEM FOR ENDOSCOPE

CROSS-REFERENCE TO RELATED APPLICATION

The present application is a continuation application of PCT/JP2016/080246 filed on Oct. 12, 2016 which is based upon and claims the benefit of priority from Japanese Patent Application No. 2015-204693 filed on Oct. 16, 2015; the entire contents of which are incorporated herein by reference.

BACKGROUND OF THE INVENTION

Field of the Invention

The present invention relates to an objective optical system for endoscope, and particularly to an objective optical system of a medical endoscope.

Description of the Related Art

An objective optical system for endoscope has a wide angle of view for observing a wide range. However, when the angle of view is widened, according to cosine fourth law, an amount of oblique incident light is degraded rapidly. Moreover, an endoscope being an equipment to be inserted into a living body, small-sizing of an inserting portion becomes indispensable. Since an objective optical system for endoscope is to be installed into the inserting portion, small-sizing of lenses becomes indispensable in an objective optical system for endoscope.

As a method to solve these issues, a method of making an optical system of a retro-focus type is available. An optical system of retro-focus type includes in order from an object side, a lens group having a negative refractive power, an aperture stop, and a lens group having a positive refractive power. By providing such arrangement, it is possible to prevent the degradation of the amount oblique incident light without making a diameter of the optical system large.

However, in an optical system of retro-focus type, a negative distortion occurs significantly. Optical systems in which the distortion is corrected are disclosed in Japanese Patent Application Laid-open Publication No. 2009-300797 and Japanese Patent Application Laid-open Publication No. Hei 11-125767.

In Japanese Patent Application Laid-open Publication No. 2009-300797, a taking lens for capsule endoscope has been disclosed. The taking lens disclosed in Japanese Patent Application Laid-open Publication No. 2009-300797 includes in order from an object side, a first lens having a negative refractive power, a second lens having a positive refractive power or a negative refractive power, an aperture stop, a third lens having a negative refractive power or a positive refractive power, a fourth lens having a positive refractive power, and a fifth lens having a positive refractive power.

In the taking lens disclosed in Japanese Patent Application Laid-open Publication No. 2009-300797, either four or six aspheric surfaces are used. In an example in which the number of aspheric surfaces is four, an aspheric surface is used for both surfaces of the first lens and both surfaces of the fifth lens. In an example in which the number of aspheric surfaces is six, an aspheric surface is used for both surfaces of the first lens, both surfaces of the second lens, and both surfaces of the fifth lens.

In Japanese Patent Application Laid-open Publication No. Hei 11-125767, a taking lens system to be used in cameras such as electronic still cameras has been disclosed. The taking lens system disclosed in Japanese Patent Application Laid-open Publication No. Hei 11-125767 includes in order from an object side, a first lens group having a negative refractive power, an aperture stop, and a second lens group having a positive refractive power.

The first lens group having a negative refractive power includes one or two negative lenses, and one positive lens. The second lens group includes a positive lens, a cemented lens, and a positive lens.

In the taking lens system in Japanese Patent Application Laid-open Publication No. Hei 11-125767, either one or two aspheric surfaces are used. In an example in which the number of aspheric surfaces is one, an aspheric surface is used for an object-side surface of a lens nearest to object. In an example in which the number of aspheric surfaces is two, an aspheric surface is used for an object-side surface of a lens nearest to object, and an object-side surface of a lens nearest to image.

SUMMARY OF THE INVENTION

An objective optical system for endoscope of the present invention comprises in order from an object side a first group having a negative refractive power, an aperture stop, and a second group having a positive refractive power, wherein the first group includes in order from the object side, a negative meniscus lens having a convex surface directed toward the object side, and a positive lens having a convex surface directed toward the object side, and the second group includes in order from the object side, a predetermined lens, a positive cemented lens, a positive single lens, or includes in order from the object side, a predetermined lens, a positive single lens, and a positive cemented lens, and the negative meniscus lens has an aspheric surface, and the predetermined lens is a meniscus lens having a convex surface directed toward an image side, and the positive cemented lens includes an object-side lens positioned on the object side and an image-side lens positioned on the image side, and the following conditional expressions (1'), (2), and (4') are satisfied:

$$0.7 < |R1/R2| < 1.1 \quad (1'),$$

$$0.6 < |R1/FL| < 3 \quad (2), \text{ and}$$

$$5 \leq |Fc/FL| \leq 7 \quad (4')$$

where,

R1 denotes a paraxial radius of curvature of a surface on the object side of the predetermined lens, R2 denotes a paraxial radius of curvature of a surface on an image side of the predetermined lens, FL denotes a focal length of the overall objective optical system for endoscope, Fc denotes a focal length at a cemented surface of the positive cemented lens, here, the focal length Fc at the cemented surface is expressed by the following expression (b)

$$Fc = Rc/(nd' - nd) \quad (b)$$

Rc denotes a paraxial radius of curvature of the cemented surface, nd denotes a refractive index of the object-side lens for a d-line, and nd' denotes a refractive index of the image-side lens for the d-line.

BRIEF DESCRIPTION OF THE DRAWINGS

FIG. 16A, FIG. 16B, FIG. 16C, FIG. 16D, and FIG. 16E are aberration diagrams of the objective optical system for endoscope according to the example 7;

FIG. 17 is a diagram showing an upper coma; and

FIG. 18 is a diagram showing a lower coma.

DETAILED DESCRIPTION OF THE INVENTION

Reasons for adopting such arrangements and effects thereof in an objective optical system for endoscope according to the present embodiment, will be described below by referring to the accompanying diagrams. However, the present invention is not restricted to the objective optical system for endoscope according to the following embodiment.

An objective optical system for endoscope of the present embodiment includes in order from an object side, a first group having a negative refractive power, an aperture stop, and a second group having a positive refractive power, wherein the first group includes in order from the object side, a negative meniscus lens having a convex surface directed toward the object side, and a positive lens having a convex surface directed toward the object side, and the second group includes in order from the object side, a predetermined lens and two positive lenses, and the negative meniscus lens has an aspheric surface, and the predetermined lens is a meniscus lens having a convex surface directed toward an image side, at least one of the two positive lenses is a cemented lens including a positive lens and a negative lens, and the following conditional expressions (1) and (2) are satisfied:

$$0.5 < |R1/R2| < 2 \quad (1), \text{ and}$$

$$0.6 < |R1/FL| < 3 \quad (2)$$

where,

R1 denotes a paraxial radius of curvature of a surface on the object side of the predetermined lens, R2 denotes a paraxial radius of curvature of a surface on an image side of the predetermined lens, and FL denotes a focal length of the overall objective optical system for endoscope.

Figure 1A:
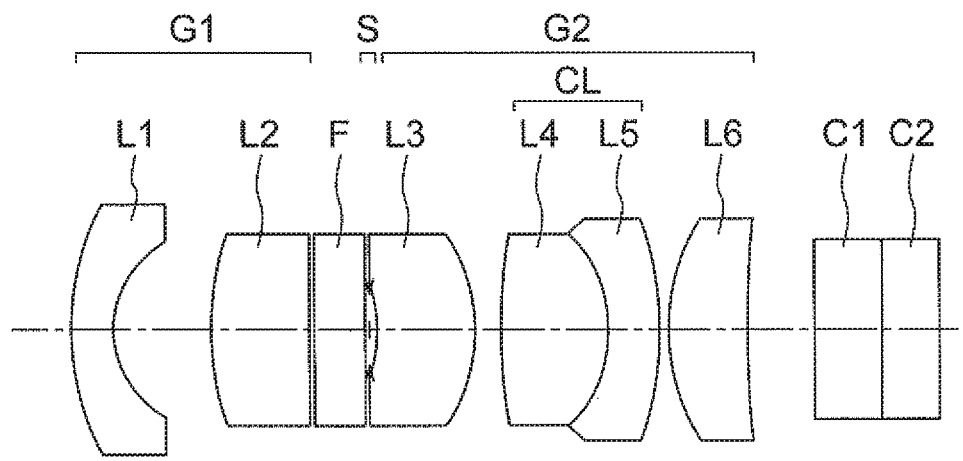
FIG. 1A is a diagram showing an objective optical system for endoscope according to a first embodiment.
Figure 1B:
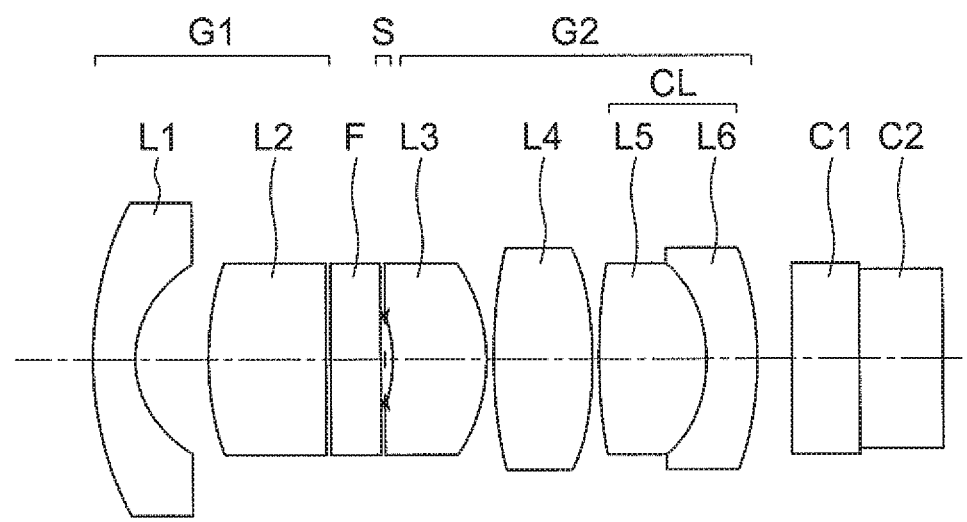
FIG. 1B is a diagram showing an objective optical system for endoscope according to a second embodiment.

The objective optical system for endoscope of the present embodiment will be described below. FIG. 1A and FIG. 1B are diagrams showing the objective optical system for endoscope of the present embodiment, where, FIG. 1A is a diagram showing an objective optical system for endoscope of a first embodiment, and FIG. 1B is a diagram showing an objective optical system for endoscope of a second embodiment.

The objective optical system for endoscope of the present embodiment is an optical system having a wide angle of view. Therefore, in the objective optical system for endoscope of the present embodiment, for securing a wide angle of view, an optical system of a retro-focus type which is appropriate for widening the angle of view, is adopted.

As shown in FIG. 1A and FIG. 1B, the objective optical system for endoscope of the first embodiment and the objective optical system for endoscope of the second embodiment include in order from an object side, a first group G1 having a negative refractive power, an aperture stop S, and a second group G2 having a positive refractive power.

Furthermore, in the objective optical system for endoscope of the present embodiment, the first group G1 includes in order from the object side, a negative meniscus lens L1 having a convex surface directed toward the object side and a positive lens L2 having a convex surface directed toward the object side. Moreover, the negative meniscus lens L1 has an aspheric surface.

In an optical system of retro-focus type, a barrel distortion occurs. As the barrel distortion occurs, an image in a peripheral portion of a field of view being compressed, it becomes difficult to observe minutely the peripheral portion of the field of view.

Moreover, in a stereoscopic-vision endoscope, when an objective optical system has a substantial distortion, in spite of a location to be observed being a flat surface, when viewed stereoscopically, an image that is seen becomes a swollen surface (convex surface) and not a flat surface. Therefore, when an attempt is made to treat a lesion part, it becomes difficult to know accurately a distance up to a lesion part. As a result, it becomes difficult to carry out the treatment in a short time.

For such reason, in the objective optical system for endoscope, it is more preferable that the barrel distortion be corrected favorably.

In the objective optical system for endoscope of the present embodiment, a height of a principal light ray becomes the maximum at the negative meniscus lens in the first group. Therefore, by making the negative refractive power small in a peripheral portion of the first meniscus lens L1, it is possible to make gentle an angle of the principal light ray emerging from the negative meniscus lens L1. Accordingly, it is possible to reduce an amount of the barrel distortion that occurs.

For such reason, in the objective optical system for endoscope of the present embodiment, an aspheric surface is used in the negative meniscus lens L1. More specifically, a shape of the aspheric surface is such that the negative refractive power in the peripheral portion of the lens surface becomes weak.

As a method for weakening the negative refractive power in the peripheral portion, a method of making the negative refractive power in the peripheral portion weaker than the negative refractive power in a central portion, and a method of making the refractive power of the peripheral portion a positive refractive power are available.

Moreover, in the objective optical system for endoscope of the present embodiment, the second group G2 includes the predetermined lens and the two positive lenses. However, the more specific arrangement of the second group G2 differs in the objective optical system for endoscope of the first embodiment and the objective optical system for endoscope of the second embodiment.

In the objective optical system for endoscope of the first embodiment, a second group G2 includes in order from an object side, a predetermined lens L3, a positive lens CL, and a positive lens L6. The predetermined lens L3 is a meniscus lens having a convex surface directed toward the image side. The positive lens CL includes a positive lens L4 and a negative lens L5.

In the objective optical system for endoscope of the second embodiment, a second group G2 includes in order from an object side, a predetermined lens L3, a positive lens L4, and a positive lens CL. The predetermined lens L3 is a meniscus lens having a convex surface directed toward the image side. The positive lens CL includes a positive lens L5 and a negative lens L6.

Moreover, in the objective optical system for endoscope of the present embodiment, a cover glass C1 and a cover glass C2 are disposed on an image side of the second group G2. An image of an object is formed on an image-side surface of the cover glass C2. Therefore, an image pickup surface of an image pickup element is positioned on the image-side surface of the cover glass C2.

As mentioned above, when the aspheric surface is used in the negative meniscus lens L1 for correcting the distortion, in the negative meniscus lens L1, the negative refractive power at the peripheral portion of the lens surface becomes smaller than the negative refractive power at the central portion of the lens surface. For instance, when the refractive power at the peripheral portion of the lens surface is let to be the positive refractive power, in the peripheral portion of the lens surface, the refractive power of the first group G1 becomes a positive refractive power and the refractive power of the second group G2 becomes a positive refractive power.

In that case, for an off-axis light beam with a large angle of view, the refractive power of the first group G1 and the refractive power of the second group G2 differ for a case of not using an aspheric surface and a case of using an aspheric surface. In the case of not using an aspheric surface, the refractive power of the first group G1 and the refractive power of the second group G2 are a positive refractive power and a negative refractive power respectively. Whereas, in the case of using the aspheric surface, both the refractive power of the first group G1 and the refractive power of the second group G2 are a positive refractive power.

In such manner, when an aspheric surface is used in the negative meniscus lens L1, for the off-axis light beam having a large angle of view, both the refractive power of the first group G1 and the refractive power of the second group G2 become a positive refractive power. Consequently, when an aspheric surface is used in the negative meniscus lens L1, it is possible to correct the distortion favorably. However, an astigmatism and a curvature of field accompanying the correction of distortion occur newly.

As one of methods for correcting the astigmatism and the curvature of field by the positive lens L2 and the predetermined lens L3, a method of disposing the positive lens L2 and the predetermined lens L3 such that a lens arrangement becomes a lens arrangement of Gaussian type is available. In the lens arrangement of Gaussian type, a pair of meniscus lenses being disposed symmetrically with an aperture stop as a line of symmetry, the astigmatism and the curvature of field are corrected favorably.

However, in an optical system of Gaussian type, each lens being a meniscus lens, it is difficult to make the refractive power large. Consequently, an optical system of Gaussian type is unfavorable for an optical system with a wide angle of view, such as endoscope, or in other words, an optical system that requires a large refractive power.

For achieving a large refractive power in an optical system of Gaussian type, any one of the positive lens L2 and the predetermined lens L3 is to be let to be a strong meniscus lens. By making such arrangement, it is possible to secure a large refractive power as well as to correct the astigmatism and the curvature of field. A strong meniscus lens is a meniscus lens for which both a radius of curvature of an object-side surface and a radius of curvature of an image-side surface are small.

However, when an arrangement as described above is made, an absolute value of the refractive power becomes asymmetric in the positive lens L2 and the predetermined lens L3, with respect to the aperture stop. Consequently, a coma including a color coma is deteriorated. This point will be described below by using FIG. 17 and FIG. 18.

FIG. 17 is a diagram showing an upper coma. FIG. 18 is a diagram showing a lower coma. The upper coma is a coma which occurs due to a light beam passing an upper side of an aperture out of the off-axis light beam, and the lower coma is a coma which occurs due to a light beam passing a lower side of an aperture out of the off-axis light beam.

Moreover, the number and shape of lenses positioned on the object side of the positive lens L2, and the number and shape of lenses positioned on the image side of the predetermined lens L3 are not determined in particular. Therefore, in FIG. 17 and FIG. 18, a lens LF and a lens LR are drawn in a simplified form as one line.

Firstly, a case in which the positive lens L2 is let to be a strong meniscus lens will be described below. In this case, as shown in FIG. 17, out of an off-axis light beam LB, a light beam LBL passing through the lower side of the aperture is focused at an image plane I. Whereas, a light beam LBU passing through the upper side of the aperture is focused on the object side of the image plane I as shown by an arrow.

In such manner, in the case in which the positive lens L2 is let to be a strong meniscus lens, an upper coma occurs. For correcting the upper coma, it is necessary to make the positive lens L2 a cemented lens for example.

However, at least two lenses are used in a cemented lens. Moreover, for correcting the coma and a chromatic aberration, each lens in the cemented lens is to be made thick to some extent. For such reason, a thickness when the positive lens L2 is let to be a cemented lens is susceptible to be more than a thickness when the positive lens L2 is let to be a single lens.

For disposing a cemented lens in the first group G1, a space necessary for the cemented lens has to be secured in the first group G1. However, as mentioned above, the thickness of the cemented lens is susceptible to be more than the thickness of the single lens. Therefore, securing the space in the first group G1 becomes difficult as compared to a case of disposing the single lens.

Furthermore, as a feature of an optical system for endoscope, the optical system for endoscope has a feature such that an angle of view is extremely wide. In an optical system with a wide angle of view, as a distance between a negative lens in a first group and an aperture stop becomes long, a light-ray height at the negative lens in the first group becomes high. As a result, an aberration is susceptible to occur. Consequently, increasing the number of lenses in the first group G1, or in other words, letting the positive lens L2 to be a cemented lens is not desirable.

Next, a case in which the predetermined lens L3 is let to be a strong meniscus lens will be described below. In this case, as shown in FIG. 18, out of an off-axis light beam LB, a light beam LBU passing the upper side of the aperture is focused at an image plane I. Whereas, a light beam LBL passing through the lower side of the aperture is focused on the object side of the image plane I as shown by an arrow.

In such manner, when the predetermined lens L3 is let to be a strong meniscus lens, the lower coma occurs. Moreover, the upper coma also occurs slightly. However, since the object-side surface of the predetermined lens L3 has a large negative refractive power, the upper coma can be corrected at the object-side surface of the predetermined lens L3.

A light-ray height becomes higher on the image side of the predetermined lens L3 than a light-ray height at the predetermined lens L3. Consequently, by disposing a positive lens on the image side of the predetermined lens L3, it is possible to correct the lower coma by this positive lens.

Therefore, in the objective optical system for endoscope of the present embodiment, the positive lens is disposed nearest to image in the second group G2. In the objective optical system for endoscope of the first embodiment, the positive lens L6 corresponds to the positive lens disposed nearest to image, and in the objective optical system for endoscope of the second embodiment, the positive lens CL corresponds to the positive lens disposed nearest to image. Accordingly, it is possible to prevent deterioration of the coma including a chromatic coma.

For disposing a positive lens nearest to image in the second group G2, a space for disposing a lens has to be secured between the second group G2 and the cover glass C1. Therefore, in the objective optical system for endoscope of the present embodiment, a meniscus shape of the predetermined lens L3 is enhanced, and the space for disposing the lens is secured.

By disposing a positive lens nearest to image in the second group G2, it is possible to correct the lower coma favorably. As a result, in the objective optical system for endoscope of the present embodiment, correction of the astigmatism, the coma, and the chromatic aberration can be carried out in a balanced manner.

Moreover, in the objective optical system for endoscope of the present embodiment, as mentioned above, conditional expressions (1) and (2) are satisfied.

When a value exceeds an upper limit value of conditional expression (1), an overall positive refractive power becomes large while the shape of the predetermined lens is a meniscus shape. Consequently, correction of the astigmatism becomes inadequate. When the value falls below a lower limit value of conditional expression (1), an overall negative refractive power becomes large while the shape of the predetermined lens is a meniscus shape. Consequently, correction of the astigmatism becomes excessive.

When a value exceeds an upper limit value of conditional expression (2), the negative refractive power of a surface on the object side of the predetermined lens becomes excessively small with respect to the focal length of the overall objective optical system for endoscope (hereinafter, referred to as 'focal length of the overall system'). In this case, since Petzval sum becomes excessively large, correction of the curvature of field is inadequate. When the value falls below a lower limit value of conditional expression (2), the negative refractive power of the surface on the object side of the predetermined lens becomes excessively large. In this case, since Petzval sum becomes excessively small, correction of the curvature of field becomes excessive.

Moreover, it is preferable that the following conditional expression (1') be satisfied instead of conditional expression (1). Furthermore, it is preferable that the following conditional expression (2') be satisfied instead of conditional expression (2).

$$0.7<|R1/R2|<1.1 \tag{1'}$$

$$0.8<|R1/FL|<1.9 \tag{2'}$$

In the objective optical system for endoscope of the present embodiment, it is preferable that the following conditional expression (3) be satisfied:

$$0.005 \leq \Delta_{ASP}/FL \leq 0.08 \tag{3}$$

where, $\Delta_{ASP}$ denotes an aspheric surface amount at a point of intersection of a principal light ray at the maximum image height and an aspheric surface, FL denotes the focal length of the overall objective optical system for endoscope, and here, the aspheric surface amount $\Delta_{ASP}$ is expressed by the following expression (a)

$$\Delta_{ASP} = \frac{c\rho^2}{1+\sqrt{1-(K+1)c^2\rho^2}} + \sum_i A_i \rho^i - \frac{c\rho^2}{1+\sqrt{1-c^2\rho^2}} \tag{a}$$

where, c denotes a reciprocal of a paraxial radius of curvature at the aspheric surface, ρ denotes a distance from an optical axis up to the point of intersection, and a distance in a plane orthogonal to the optical axis including the point of intersection, K denotes a conical coefficient, and $A_i$ denotes an aspherical coefficient.

When a value exceeds an upper limit value of conditional expression (3), the aspheric surface amount with respect to the focal length of the overall system becomes excessively large. Consequently, the curvature of field cannot be corrected favorably. When the value falls below a lower limit value of conditional expression (3), the aspheric surface amount with respect to the focal length of the overall system becomes excessively small. Consequently, the distortion cannot be corrected favorably.

It is more preferable that the following conditional expression (3') be satisfied instead of conditional expression (3)

$$0.02 \leq A_{ASP}/FL \leq 0.04 \tag{3'}$$

In the objective optical system for endoscope of the present embodiment, it is preferable that one of the positive lens and the negative lens in the cemented lens be an object-side lens positioned on the object side, and the other is an image-side lens positioned on the image side, and the following conditional expression (4) be satisfied:

$$4 \leq |Fc/FL| \leq 20 \tag{4}$$

where,

Fc denotes a focal length at the cemented surface of the cemented lens,

FL denotes the focal length of the overall objective optical system for endoscope, here, the focal length Fc at the cemented surface is expressed by the following expression (b)

$$Fc = Rc/(nd' - nd) \tag{b}$$

where,

Rc denotes a paraxial radius of curvature of the cemented surface, nd denotes a refractive index of the object-side lens for the d-line, and nd' denotes a refractive index of the image-side lens for the d-line.

When a value exceeds an upper limit value of conditional expression (4), the refractive power of the cemented surface with respect to the focal length of the overall system becomes excessively small. Consequently, the curvature of field cannot be corrected favorably. When the value falls below a lower limit value of conditional expression (4), the refractive power of the cemented surface with respect to the focal length of the overall system becomes excessively large. Consequently, correction of the coma and correction of the curvature of field become excessive.

It is more preferable that the following conditional expression (4') be satisfied instead of conditional expression (4).

$$5 \leq |Fc/FL| \leq 7 \tag{4'}$$

In the objective optical system for endoscope of the present embodiment, it is preferable that the two positive lenses are a cemented lens and a single lens, and the following conditional expression (5) be satisfied:

$$1.5 \leq |Fr/Ff| \leq 5 \tag{5}$$

where,

Ff denotes a focal length of a negative meniscus lens having the convex surface directed toward the object side, and Fr denotes a focal length of the single lens.

When a value falls below a lower limit value of conditional expression (5), the negative meniscus lens having the convex surface directed toward the object side becomes large, and is not suited for the objective optical system for endoscope. When the value exceeds an upper limit value of conditional expression (5), correction of the barrel distortion becomes difficult.

It is more preferable that the following conditional expression (5') be satisfied instead of conditional expression (5).

$$3 \leq |Fr/Ff| \leq 4 \tag{5'}$$

Moreover, in the objective optical system for endoscope of the present embodiment, it is preferable that the two positive lenses in the second group be disposed in order of a cemented lens of a positive lens and a negative lens, and a positive lens, and with this arrangement, to satisfy conditional expression (5) or (5').

As described heretofore, in the objective optical system for endoscope of the present embodiment, the distortion is corrected favorably. Therefore, it is possible to use the objective optical system for endoscope of the present embodiment for an objective optical system of a stereoscopic-vision endoscope.

As mentioned above, in a stereoscopic-vision endoscope, when the objective optical system has a substantial distortion, in spite of the location to be observed being a flat surface, when viewed stereoscopically, an image that is seen becomes a swollen surface (convex surface) and not a flat surface.

However, in the objective optical system for endoscope of the present embodiment, the distortion is corrected favorably. Therefore, in a stereoscopic-vision endoscope using the objective optical system for endoscope of the present embodiment, it is possible to know accurately the distance up to a lesion part. Therefore, in a case of carrying out a treatment of a lesion part, it is possible to carry out the treatment efficiently.

Figure 2:
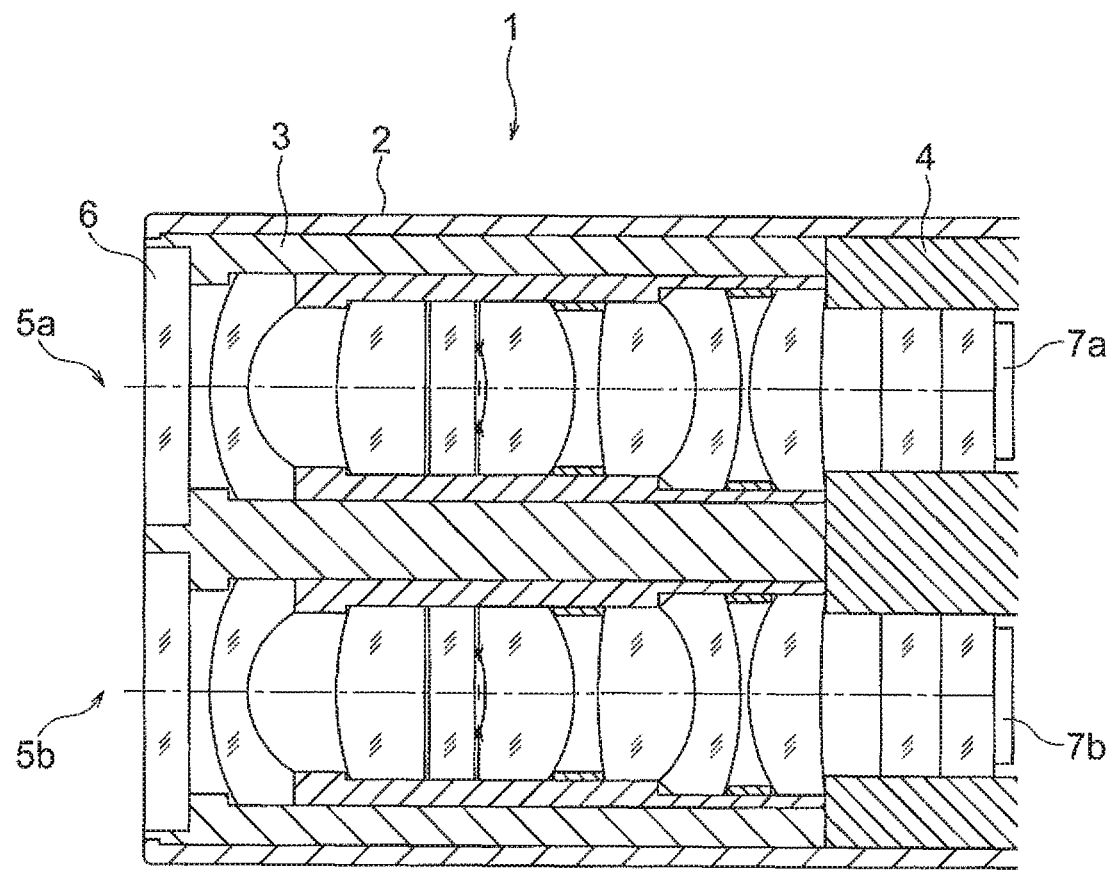
FIG. 2 is a diagram in which an objective optical system according to the present embodiment is applied to an optical system of a stereoscopic-vision endoscope.

FIG. 2 is a diagram showing a front-end portion of a stereoscopic-vision endoscope of the present embodiment. A front-end portion 1 includes a front-end member 2, an objective unit 3, and an image pickup unit 4. An interior of the front-end member 2 is provided with a circular cylindrical shaped through hole, and the objective unit 3 and the image pickup unit 4 are fitted into the through hole.

Two objective optical systems 5a and 5b are disposed in the objective unit 3. In FIG. 2, the objective optical system for endoscope of the first embodiment is used for each of the two objective optical systems 5a and 5b. Moreover, a plane parallel plate 6 is disposed nearest to object of the two objective optical systems 5a and 5b. The plane parallel plate 6 is sapphire for example.

Since sapphire is an extremely hard material, the sapphire is strong against an external impact. Therefore, a lens surface on the object side is hard to be scratched. By using sapphire, a projection of a scratch on image and an occurrence of flare due to the scratch are hard to occur. A glass material of the negative lens is not restricted to sapphire. When a crystalline material having a high hardness is used for the plane parallel plate 6, a surface of the lens is hardly scratched.

Moreover, sapphire is highly resistant to moisture vapor. Therefore, a cemented portion of the plane parallel plate 6 and the objective unit 3 is to be cemented to be airtight by brazing and soldering. By making such arrangement, it is possible to make an internal space of the objective unit 3 an airtight space. As a result, even when autoclave sterilization is carried out, a high-pressure steam does not enter at all into the objective unit 3.

Two CCDs (charge coupled devices) 7a and 7b are disposed in the image pickup unit 4. A center of an image pickup surface of the CCD 7a is disposed at a position shifted in an upward direction in a paper surface from an optical axis of the objective optical system 5a. A center of an image pickup surface of the CCD 7b is disposed at a position shifted in a downward direction in the paper surface from an optical axis of the objective optical system 5b.

An amount of shift of the CCD 7a and an amount of shift of the CCD 7b are same. Accordingly, there is a parallax between an image acquired by the CCD 7a and an image acquired by the CCD 7b. As a result, a stereoscopic vision becomes possible.

As mentioned above, the objective optical system for endoscope of the first embodiment is used for each of the two objective optical systems 5a and 5b. Therefore, according to the stereoscopic-vision endoscope of the present embodiment, even in a case in which a flat surface is viewed stereoscopically, it can be identified as a flat surface. As a result, it is possible to know accurately the distance up to an object to be observed.

Examples will be described below.

FIG. 4A, FIG. 6A, FIG. 8A, FIG. 10A, FIG. 12A, FIG. 14A, and FIG. 16A show a spherical aberration (SA). FIG. 4B, FIG. 6B, FIG. 8B, FIG. 10B, FIG. 12B, FIG. 14B, and FIG. 16B show an astigmatism (AS). FIG. 4C, FIG. 6C, FIG. 8C, FIG. 10C, FIG. 12C, FIG. 14C, and FIG. 16C show a distortion (DT). FIG. 4D, FIG. 6D, FIG. 8D, FIG. 10D, FIG. 12D, FIG. 14D, and FIG. 16D show a chromatic aberration of magnification (CC).

In aberration diagrams, a horizontal axis indicates an aberration amount. For the spherical aberration, the astigmatism, the coma, and the chromatic aberration of magnification, the unit of aberration amount is mm. Moreover, for the distortion, the unit of aberration amount is %. Furthermore, ω denotes a half angle of view and the unit thereof is °, and FNO denotes an F-number. The unit of a wavelength of an aberration curve is nm.

In an aberration diagram of the coma, a vertical axis indicates an aperture ratio. An aberration curve in an X-direction (meridional direction) is indicated by a thin line, and an aberration curve in a Y-direction (sagittal direction) is indicated by a thick line.

In each of the following examples, a negative meniscus lens having a convex surface directed toward an object side is disposed nearest to object of an objective optical system for endoscope. However, as shown in FIG. 2, a plane parallel plate such as sapphire may be disposed on the object side of the negative meniscus lens.

Example 1

Figure 3:
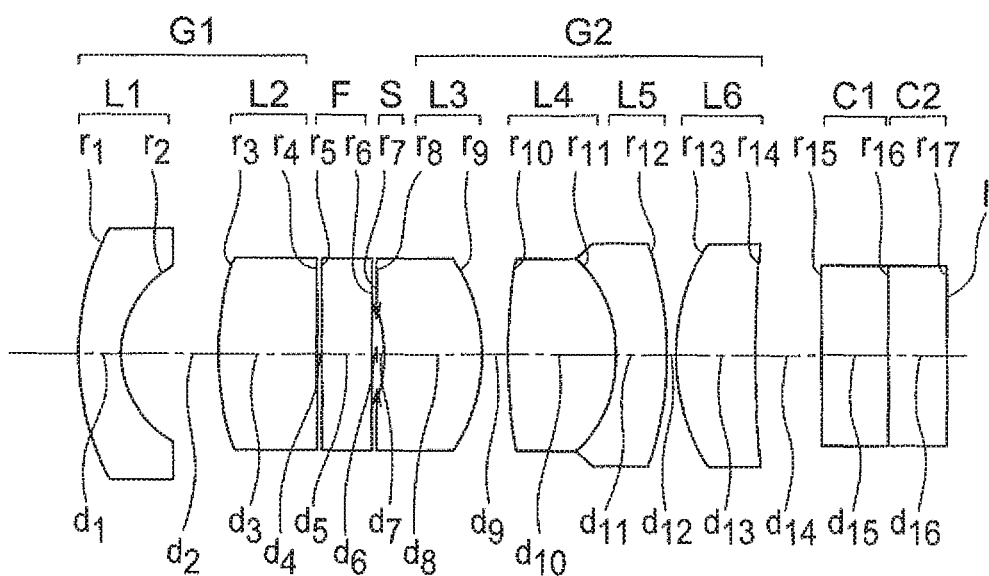
FIG. 3 is a diagram showing a cross-sectional view of an arrangement of an objective optical system for endoscope according to an example 1.
Figure 4:
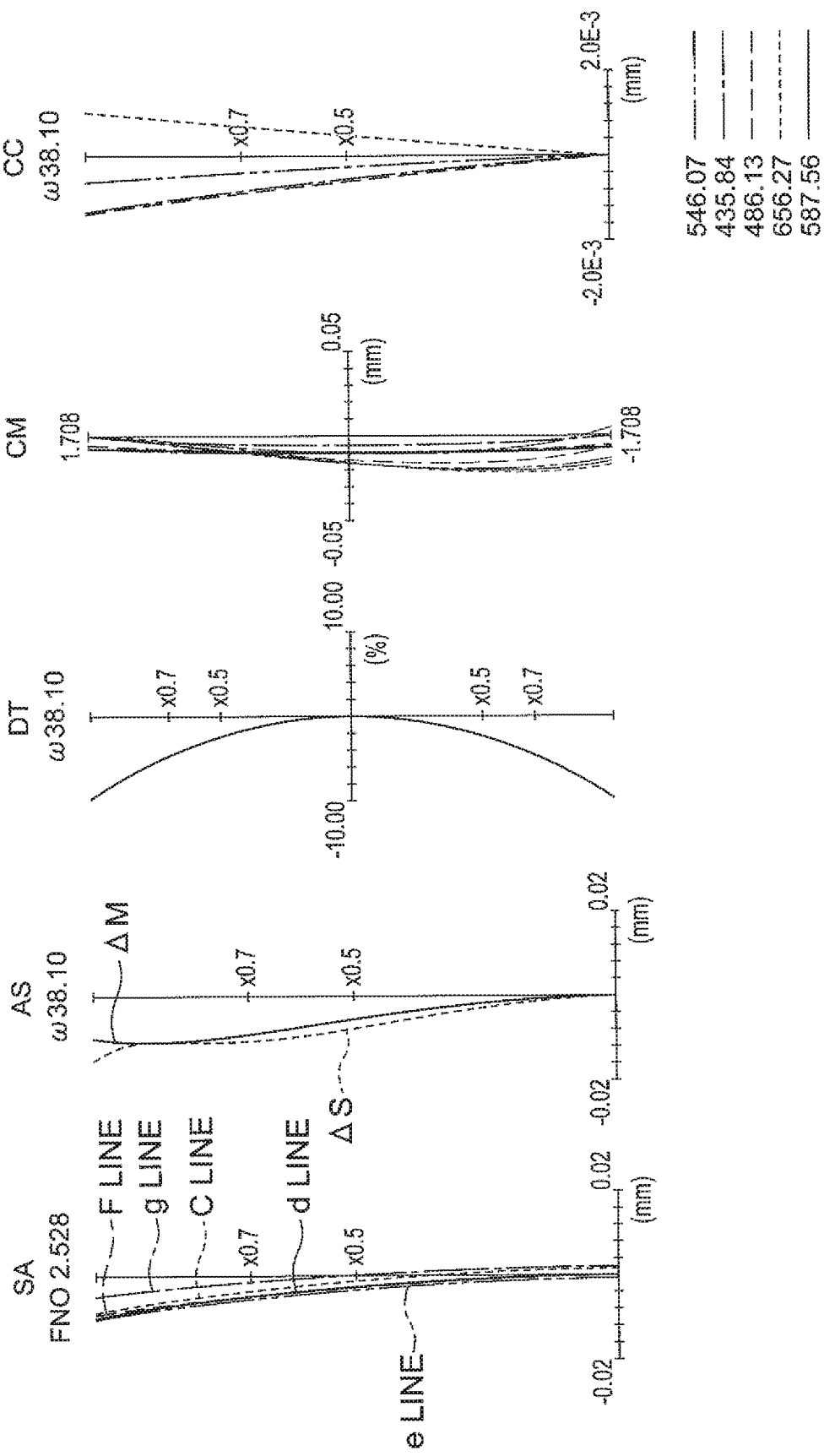
FIG. 4A, FIG. 4B, FIG. 4C, FIG. 4D, and FIG. 4E are aberration diagrams of the objective optical system for endoscope according to the example 1.

An objective optical system for endoscope according to an example 1 will be described below. FIG. 3 is a diagram showing a cross-sectional view of an arrangement of the objective optical system for endoscope according to the example 1. Moreover, FIG. 4A, FIG. 4B, FIG. 4C, FIG. 4D, and FIG. 4E are aberration diagrams of the objective optical system for endoscope according to the example 1.

The objective optical system for endoscope of the example 1, as shown in FIG. 3, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a biconvex positive lens L4, a negative meniscus lens L5 having a convex surface directed toward the image side, and a positive meniscus lens L6 having a convex surface directed toward the object side. The biconvex positive lens L4 and the negative meniscus lens L5 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 2

Figure 5:
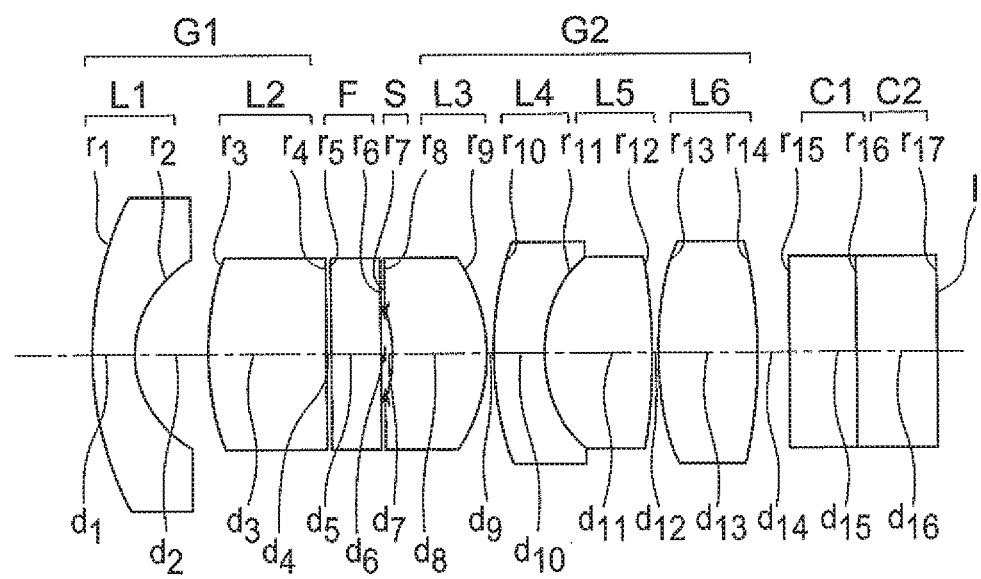
FIG. 5 is a diagram showing a cross-sectional view of an arrangement of an objective optical system for endoscope according to an example 2.
Figure 6:
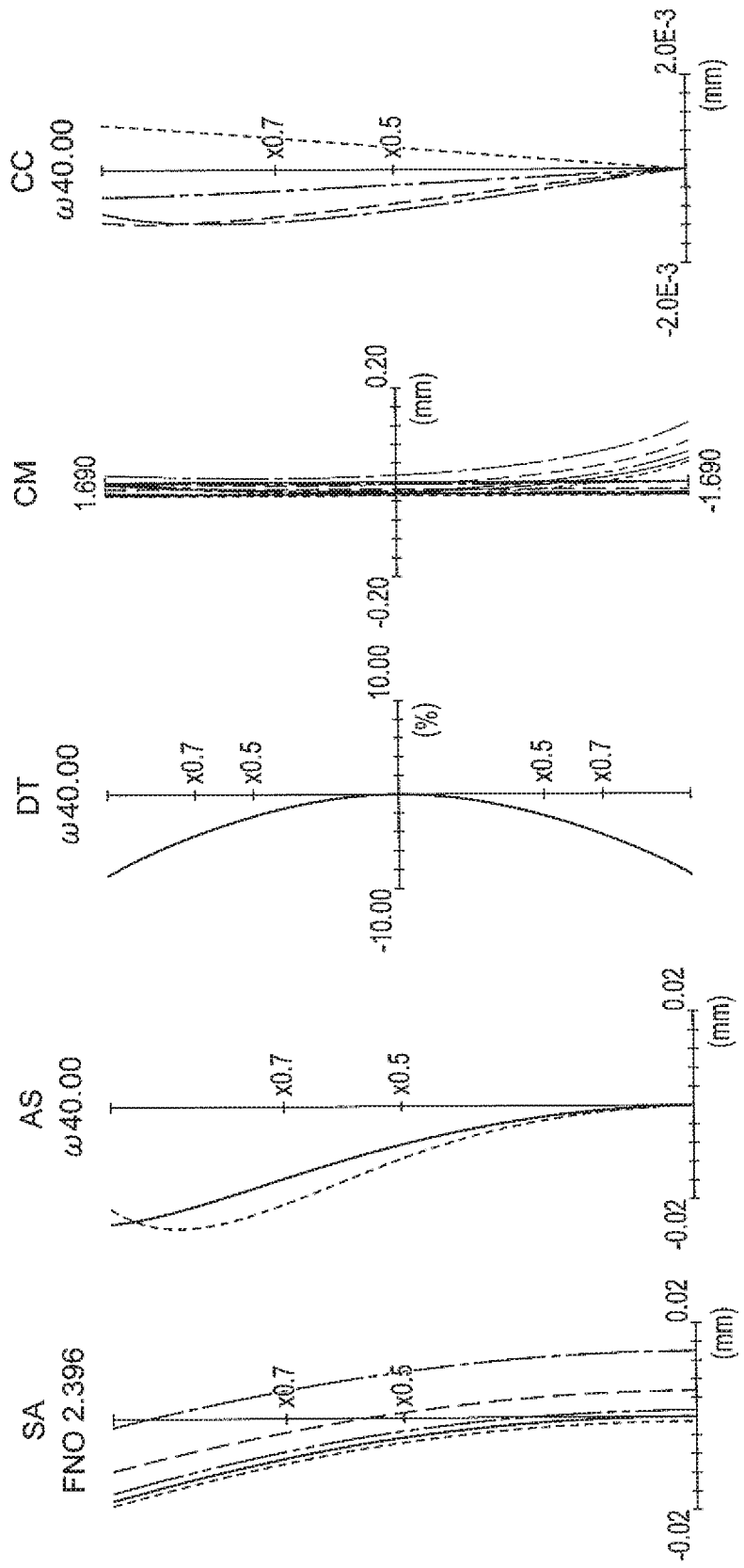
FIG. 6A, FIG. 6B, FIG. 6C, FIG. 6D, and FIG. 6E are aberration diagrams of the objective optical system for endoscope according to the example 2.

An objective optical system for endoscope according to an example 2 will be described below. FIG. 5 is a diagram showing a cross-sectional view of an arrangement of the objective optical system for endoscope according to the example 2. Moreover, FIG. 6A, FIG. 6B, FIG. 6C, FIG. 6D, and FIG. 6E are aberration diagrams of the objective optical system for endoscope according to the example 2.

The objective optical system for endoscope of the example 2, as shown in FIG. 5, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a negative meniscus lens L4 having a convex surface directed toward the object side, a biconvex positive lens L5, and a biconvex positive lens L6. The negative meniscus lens L4 and the biconvex positive lens L5 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 3

Figure 7:
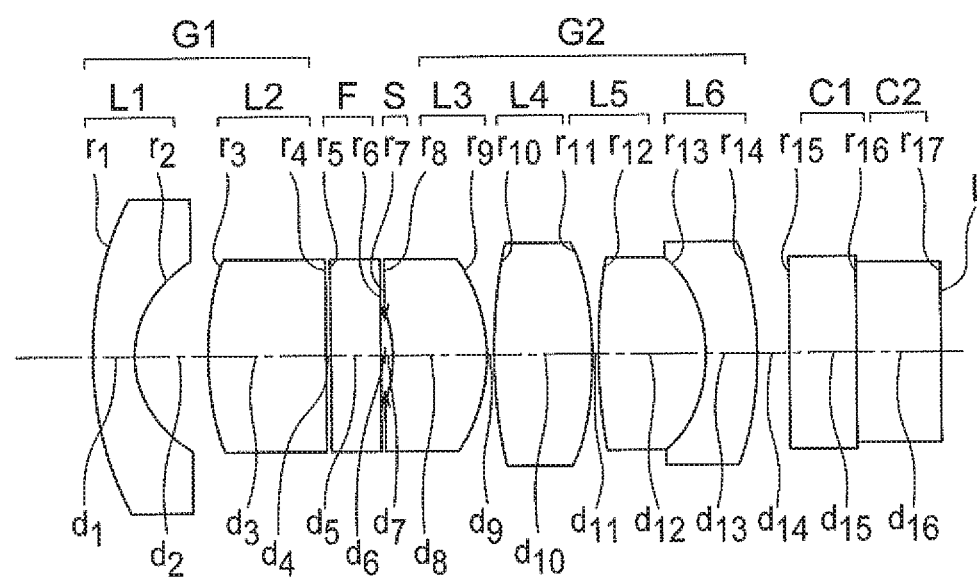
FIG. 7 is a diagram showing a cross-sectional view of an arrangement of an objective optical system for endoscope according to an example 3.
Figure 8:
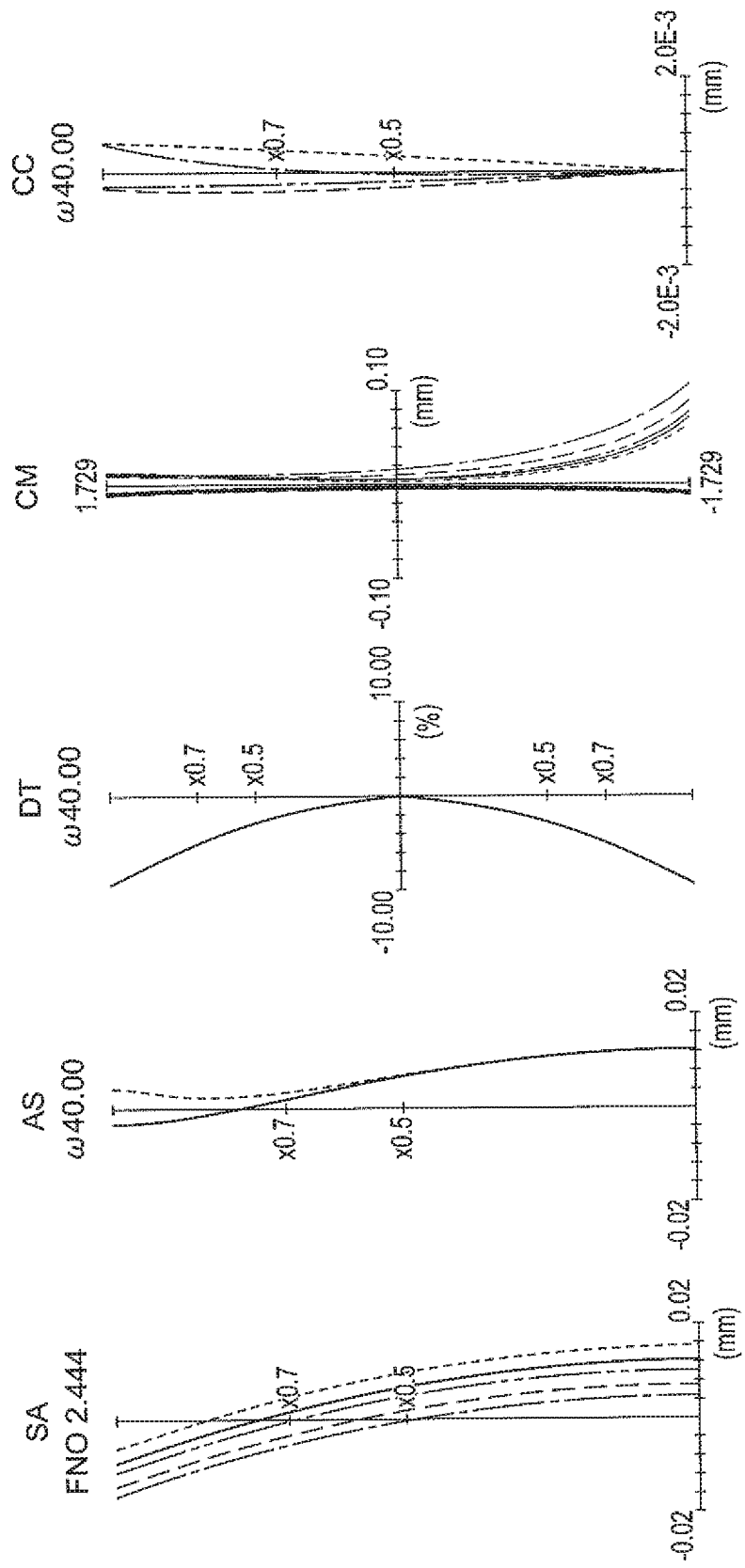
FIG. 8A, FIG. 8B, FIG. 8C, FIG. 8D, and FIG. 8E are aberration diagrams of the objective optical system for endoscope according to the example 3.

An objective optical system for endoscope according to an example 3 will be described below. FIG. 7 is a diagram showing a cross-sectional view of an arrangement of the objective optical system for endoscope according to the example 3. Moreover, FIG. 8A, FIG. 8B, FIG. 8C, FIG. 8D, and FIG. 8E are aberration diagrams of the objective optical system for endoscope according to the example 3.

The objective optical system for endoscope of the example 3, as shown in FIG. 7, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a biconvex positive lens L4, a biconvex positive lens L5, and a negative meniscus lens L6 having a convex surface directed toward the image side. The biconvex positive lens L5 and the negative meniscus lens L6 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 4

Figure 9:
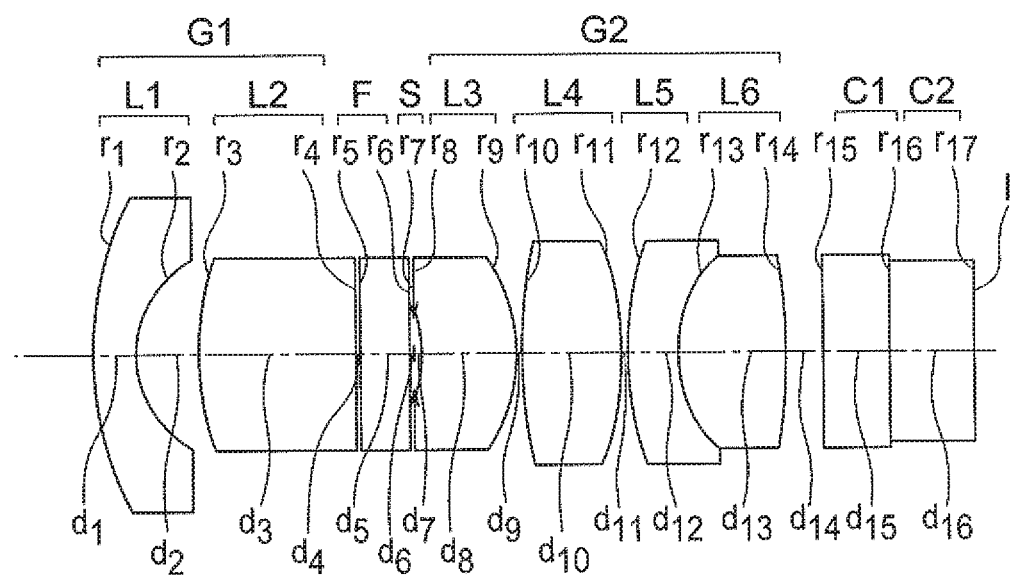
FIG. 9 is a diagram showing a cross-sectional view of an arrangement of an objective optical system for endoscope according to an example 4.
Figure 10:
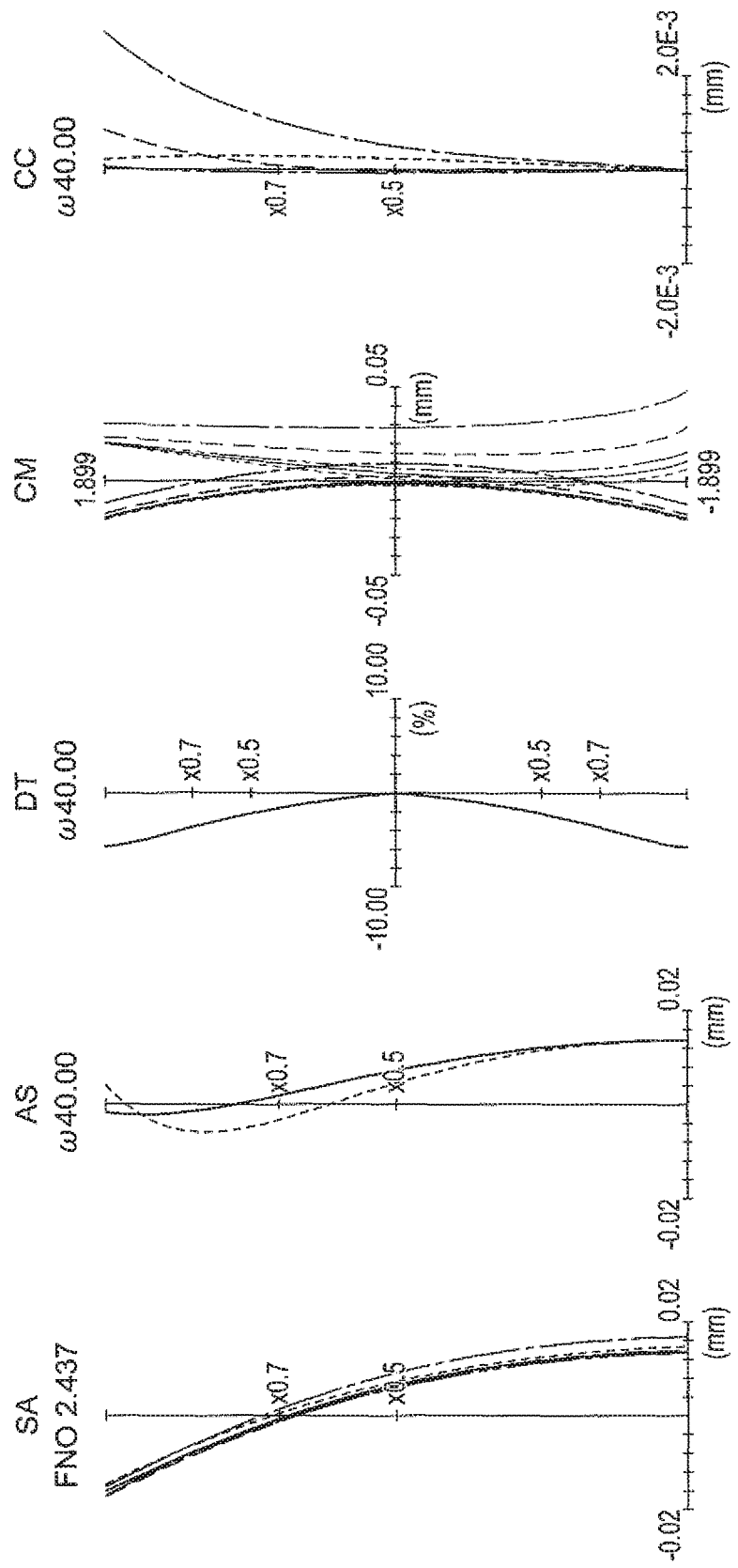
FIG. 10A, FIG. 10B, FIG. 10C, FIG. 10D, and FIG. 10E are aberration diagrams of the objective optical system for endoscope according to the example 4.

An objective optical system for endoscope according to an example 4 will be described below. FIG. 9 is a diagram showing a cross-sectional view of an arrangement of the objective optical system for endoscope according to the example 4. Moreover, FIG. 10A, FIG. 10B, FIG. 10C, FIG. 10D, and FIG. 10E are aberration diagrams of the objective optical system for endoscope according to the example 4.

The objective optical system for endoscope of the example 4, as shown in FIG. 9, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a biconvex positive lens L4, a negative meniscus lens L5 having a convex surface directed toward the object side, and a biconvex positive lens L6. The negative meniscus lens L5 and the biconvex positive lens L6 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 5

Figure 11:
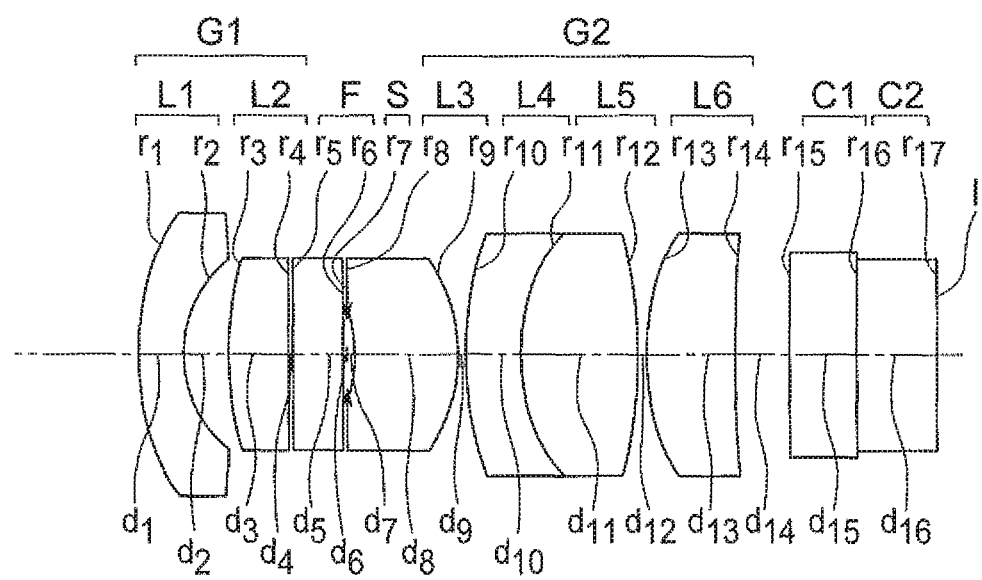
FIG. 11 is a diagram showing a cross-sectional view of an arrangement of an objective optical system for endoscope according to an example 5.
Figure 12:
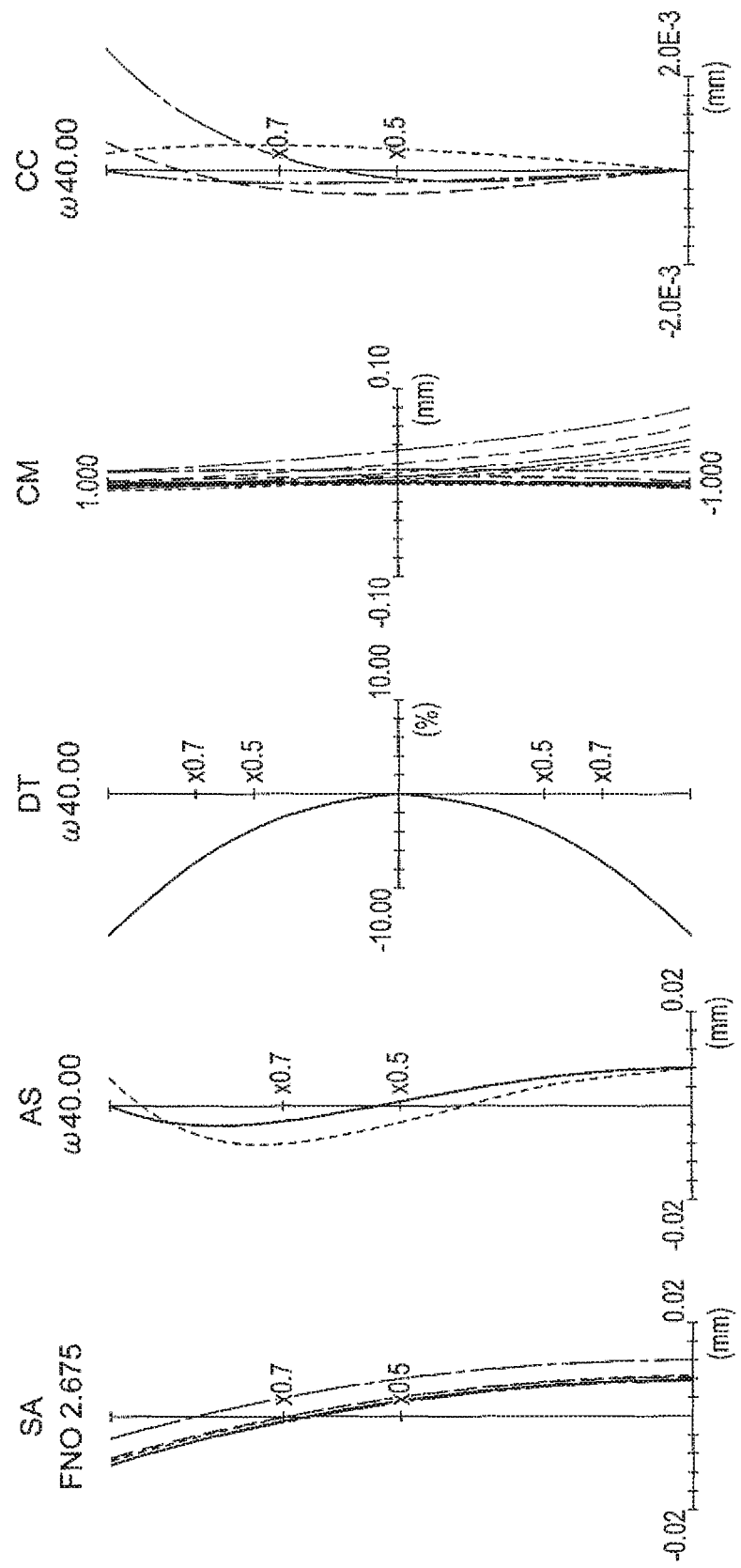
FIG. 12A, FIG. 12B, FIG. 12C, FIG. 12D, and FIG. 12E are aberration diagrams of the objective optical system for endoscope according to the example 5.

An objective optical system for endoscope according to an example 5 will be described below. FIG. 11 is a diagram showing a cross-sectional view of an arrangement of the objective optical system for endoscope according to the example 5. Moreover, FIG. 12A, FIG. 12B, FIG. 12C, FIG. 12D, and FIG. 12E are aberration diagrams of the objective optical system for endoscope according to the example 5.

The objective optical system for endoscope of the example 5, as shown in FIG. 11, includes in order from an object side, a first group G1 having a negative refractive power, an aperture stop S, and a second group G2 having a positive refractive power.

The first group G1 includes a negative meniscus lens L1 having a convex surface directed toward the object side and a positive meniscus lens L2 having a convex surface directed toward the object side. An aspheric surface is provided to an object-side surface of the negative meniscus lens L1.

The second group G2 includes a positive meniscus lens L3 having a convex surface directed toward an image side, a negative meniscus lens L4 having a convex surface directed toward the object side, a biconvex positive lens L5, and a positive meniscus lens L6 having a convex surface directed toward the object side. The negative meniscus lens L4 and the biconvex positive lens L5 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 6

Figure 13:
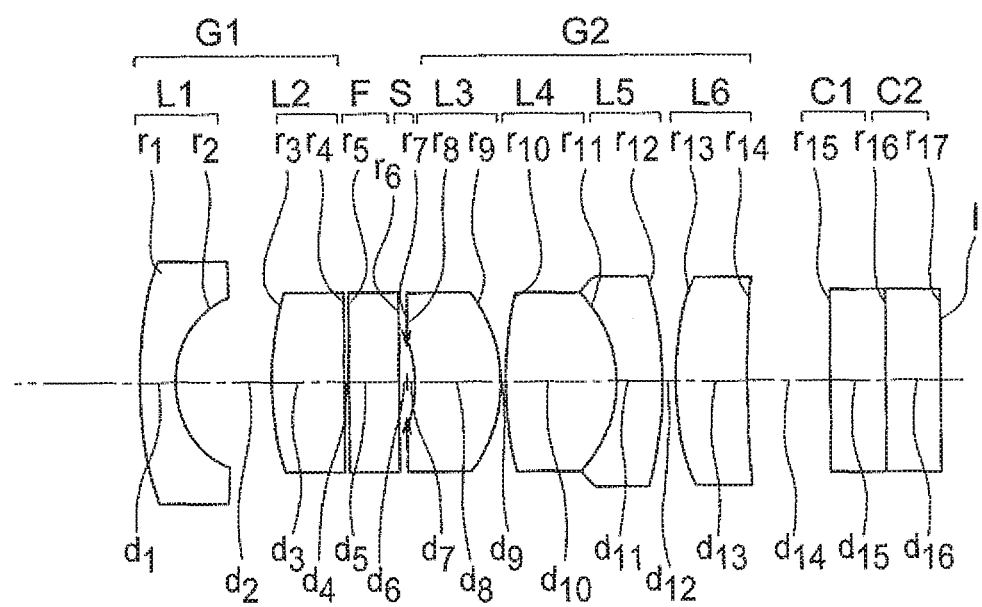
FIG. 13 is a diagram showing a cross-sectional view of an arrangement of an objective optical system for endoscope according to an example 6.
Figure 14:
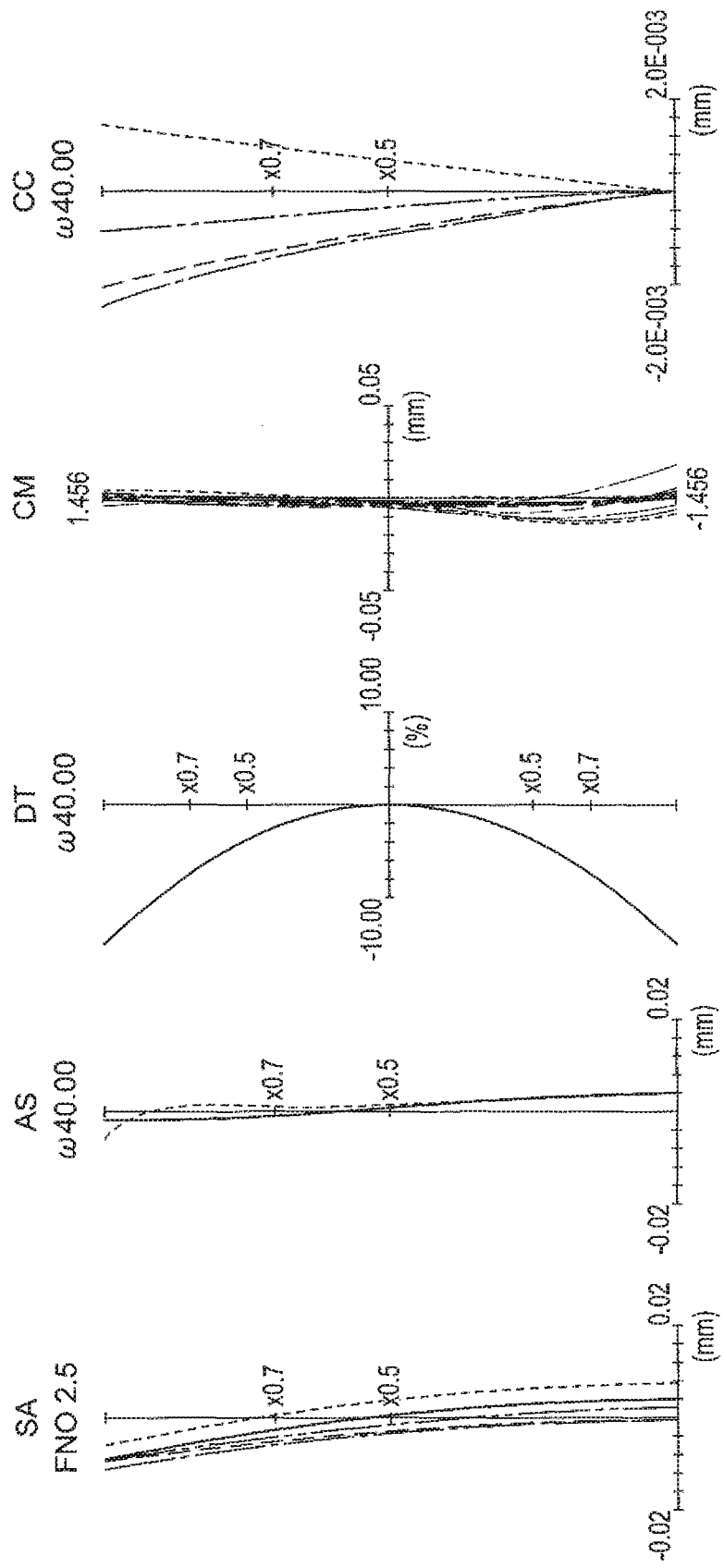
FIG. 14A, FIG. 14B, FIG. 14C, FIG. 14D, and FIG. 14E are aberration diagrams of the objective optical system for endoscope according to the example 6.

An objective optical system for endoscope according to an example 6 will be described below. FIG. 13 is a diagram showing a cross-sectional view of an arrangement of the objective optical system for endoscope according to the example 6. Moreover, FIG. 14A, FIG. 14B, FIG. 14C, FIG. 14D, and FIG. 14E are aberration diagrams of the objective optical system for endoscope according to the example 6.

The objective optical system for endoscope of the example 6, as shown in FIG. 13, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a biconvex positive lens L4, a negative meniscus lens L5 having a convex surface directed toward the image side, and a positive meniscus lens L6 having a convex surface directed toward the object side. The biconvex positive lens L4 and the negative meniscus lens L5 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Example 7

Figure 15:
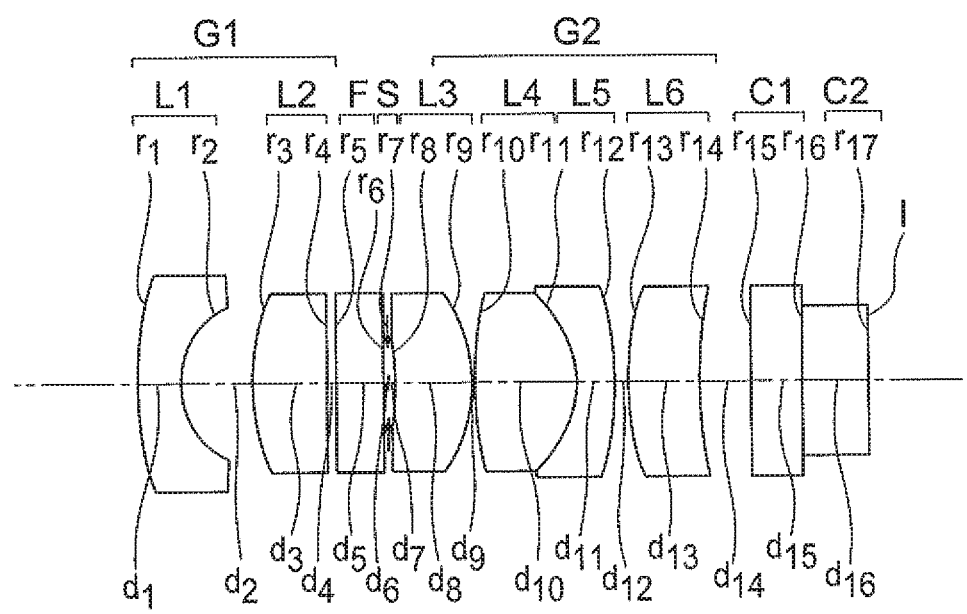
FIG. 15 is a diagram showing a cross-sectional view of an arrangement of an objective optical system for endoscope according to an example 7.

An objective optical system for endoscope according to an example 7 will be described below. FIG. 15 is a diagram showing a cross-sectional view of an arrangement of the objective optical system for endoscope according to the example 7. Moreover, FIG. 16A, FIG. 16B, FIG. 16C, FIG. 16D, and FIG. 16E are aberration diagrams of the objective optical system for endoscope according to the example 7.

The objective optical system for endoscope of the example 7, as shown in FIG. 15, includes in order from an object side, a first group G1 having a negative refractive power, an aperture stop S, and a second group G2 having a positive refractive power.

The first group G1 includes a negative meniscus lens L1 having a convex surface directed toward the object side and a planoconvex positive lens L2 having a convex surface directed toward the object side. An aspheric surface is provided to an object-side surface of the negative meniscus lens L1.

The second group G2 includes a positive meniscus lens L3 having a convex surface directed toward an image side, a biconvex positive lens L4, a negative meniscus lens L5 having a convex surface directed toward the image side, and a positive meniscus lens L6 having a convex surface directed toward the object side. The biconvex positive lens L4 and the negative meniscus lens L5 form a cemented lens having a positive refractive power. Moreover, the positive meniscus lens L3 is the predetermined lens.

An optical filter F is disposed between the first group G1 and the second group G2. Moreover, a cover glass C1 and a cover glass C2 are disposed on the image side of the second group G2. The cover glass C2 is a cover glass of a solid image pickup element.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, * denotes an aspherical surface, FL denotes a focal length of the overall objective optical system for endoscope, FNO. denotes an F number, ω denotes a half angle of view, Δ denotes a point of intersection (aspheric surface amount) of a principal light ray with the maximum image height and an aspheric surface.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+$$

Further, in the aspherical surface coefficients, 'E-n' (where, n is an integral number) indicates '$10^{-n}$'. Moreover, these symbols are commonly used in the following numerical data for each example.

Example 1

Unit mm

Surface data

| Surface no. | r | d | nd | vd |
|---|---|---|---|---|
| 1* | 2.2851 | 0.25 | 1.80610 | 40.92 |
| 2 | 0.639 | 0.595 | | |
| 3 | 1.961 | 0.6 | 2.00330 | 28.27 |
| 4 | ∞ | 0.03 | | |
| 5 | ∞ | 0.3 | 1.52134 | 74.98 |
| 6 | ∞ | 0.03 | | |
| 7 (Stop) | ∞ | 0.045 | | |
| 8 | −1.02 | 0.6 | 2.00330 | 28.27 |
| 9 | −1.132 | 0.16 | | |
| 10 | 4.021 | 0.65 | 1.72916 | 54.68 |
| 11 | −0.856 | 0.3 | 1.92286 | 18.90 |
| 12 | −2.297 | 0.06 | | |
| 13 | 1.354 | 0.48 | 1.51633 | 64.14 |
| 14 | 6.202 | 0.408 | | |
| 15 | ∞ | 0.4 | 1.51633 | 64.14 |
| 16 | ∞ | 0.35 | 1.51633 | 64.14 |
| 17 (Image plane) | ∞ | | | |

Aspherical surface data
1st surface k = 0.0000
A4 = 1.2173E−01, A6 = −5.6561E−02, A8 = 6.7563E−02

Various data

| FNO. | 2.2 |
|---|---|
| ω | 38 |
| FL | 0.726 |
| Δ | 0.6267 |

Example 2

Unit mm

Surface data

| Surface no. | r | d | nd | vd |
|---|---|---|---|---|
| 1* | 3.3748 | 0.25 | 1.80610 | 40.92 |
| 2 | 0.6422 | 0.4333 | | |
| 3 | 1.9787 | 0.712 | 2.00330 | 28.27 |
| 4 | ∞ | 0.03 | | |
| 5 | ∞ | 0.3 | 1.52300 | 75.00 |
| 6 | ∞ | 0.03 | | |
| 7 (Stop) | ∞ | 0.045 | | |
| 8 | −1.1773 | 0.567 | 2.00330 | 28.27 |
| 9 | −1.2097 | 0.04 | | |
| 10 | 2.4915 | 0.3 | 1.92286 | 18.90 |
| 11 | 0.8095 | 0.65 | 1.72916 | 54.68 |
| 12 | −2.5904 | 0.04 | | |
| 13 | 2.0279 | 0.6 | 1.51633 | 64.14 |
| 14 | −3.2054 | 0.2215 | | |
| 15 | ∞ | 0.4 | 1.51633 | 64.14 |
| 16 | ∞ | 0.5 | 1.50510 | 63.26 |
| 17 (Image plane) | ∞ | | | |

Aspherical surface data
1st surface k = 0.0000
A4 = 1.5390E−01, A6 = −6.8858E−02, A8 = 4.5761E−02

Various data

| FNO | 2.5 |
|---|---|
| ω | 40 |
| FL | 0.669 |
| Δ | 0.6073 |

Example 3

Unit mm

Surface data

| Surface no. | r | d | nd | vd |
|---|---|---|---|---|
| 1* | 3.4949 | 0.25 | 1.80610 | 40.92 |
| 2 | 0.6385 | 0.4397 | | |
| 3 | 1.9757 | 0.7184 | 2.00330 | 28.27 |
| 4 | ∞ | 0.03 | | |
| 5 | ∞ | 0.3 | 1.52300 | 75.00 |
| 6 | ∞ | 0.03 | | |
| 7 (Stop) | ∞ | 0.045 | | |
| 8 | −1.1755 | 0.5685 | 2.00330 | 28.27 |
| 9 | −1.2113 | 0.04 | | |
| 10 | 3.2658 | 0.6 | 1.51633 | 64.14 |
| 11 | −2.033 | 0.04 | | |
| 12 | 2.6789 | 0.65 | 1.72916 | 54.68 |
| 13 | −0.809 | 0.3 | 1.92286 | 18.90 |
| 14 | −2.5448 | 0.208 | | |
| 15 | ∞ | 0.4 | 1.51633 | 64.14 |
| 16 | ∞ | 0.5 | 1.50510 | 63.26 |
| 17 (Image plane) | ∞ | | | |

Aspherical surface data
1st surface k = 0.0000
A4 = 1.43E−01, A6 = −6.62E−02, A8 = 5.10E−02

Various data

| FNO | 2.5 |
|---|---|
| ω | 40 |
| FL | 0.674 |
| Δ | 0.5968 |

Example 4

Unit mm

Surface data

| Surface no. | r | d | nd | vd |
|---|---|---|---|---|
| 1* | 3.5668 | 0.25 | 1.80610 | 40.92 |
| 2 | 0.6392 | 0.3715 | | |
| 3 | 2.2797 | 0.9638 | 2.00330 | 28.27 |
| 4 | ∞ | 0.03 | | |
| 5 | ∞ | 0.3 | 1.52300 | 75.00 |
| 6 | ∞ | 0.03 | | |
| 7 (Stop) | ∞ | 0.045 | | |
| 8 | −1.1913 | 0.5576 | 2.00330 | 28.27 |
| 9 | −1.1881 | 0.04 | | |
| 10 | 3.5003 | 0.6 | 1.51633 | 64.14 |
| 11 | −2.2785 | 0.04 | | |
| 12 | 2.0606 | 0.3 | 1.92286 | 18.90 |
| 13 | 0.7289 | 0.65 | 1.72916 | 54.68 |
| 14 | −2.9369 | 0.2335 | | |
| 15 | ∞ | 0.4 | 1.51633 | 64.14 |
| 16 | ∞ | 0.5 | 1.50510 | 63.26 |
| 17 (Image plane) | ∞ | | | |

Aspherical surface data
1st surface k = 0.0000
A4 = 1.6214E−01, A6 = −7.1307E−02, A8 = 5.2423E−02

-continued

Unit mm

Various data

| FNO | 2.5 |
|---|---|
| ω | 40 |
| FL | 0.647 |
| Δ | 0.6348 |

Example 5

Unit mm

Surface data

| Surface no. | r | d | nd | vd |
|---|---|---|---|---|
| 1* | 1.7317 | 0.25 | 1.80610 | 40.92 |
| 2 | 0.6946 | 0.28 | | |
| 3 | 2.0912 | 0.3256 | 1.92286 | 18.90 |
| 4 | 8.5982 | 0.03 | | |
| 5 | ∞ | 0.3 | 1.52300 | 75.00 |
| 6 | ∞ | 0.03 | | |
| 7 (Stop) | ∞ | 0.045 | | |
| 8 | −0.6157 | 0.612 | 1.81600 | 46.62 |
| 9 | −0.8459 | 0.04 | | |
| 10 | 2.4281 | 0.3 | 1.92286 | 18.90 |
| 11 | 0.972 | 0.7 | 1.72916 | 54.68 |
| 12 | −2.5764 | 0.04 | | |
| 13 | 1.3415 | 0.5244 | 1.51633 | 64.14 |
| 14 | 21.8823 | 0.282 | | |
| 15 | ∞ | 0.4 | 1.51633 | 64.14 |
| 16 | ∞ | 0.5 | 1.51633 | 64.14 |
| 17 (Image plane) | ∞ | | | |

Aspherical surface data
1st surface k = 0.0000
A4 = 9.8950E−02, A6 = −1.9271E−02, A8 = 6.5321E−02

Various data

| FNO | 2.5 |
|---|---|
| ω | 40 |
| FL | 0.759 |
| Δ | 0.5578 |

Example 6

Unit mm

Surface data

| Surface no. | r | d | nd | vd |
|---|---|---|---|---|
| 1* | 3.9113 | 0.2875 | 1.80610 | 40.92 |
| 2 | 0.7315 | 0.7068 | | |
| 3 | 2.1993 | 0.5667 | 1.84666 | 23.78 |
| 4 | ∞ | 0.0546 | | |
| 5 | ∞ | 0.3696 | 1.52300 | 75.00 |
| 6 | ∞ | 0.0547 | | |
| 7 (Stop) | ∞ | 0.0805 | | |
| 8 | −1.3843 | 0.6377 | 1.84666 | 23.78 |
| 9 | −1.328 | 0.0454 | | |
| 10 | 3.1708 | 0.8531 | 1.72916 | 54.68 |
| 11 | −1.0147 | 0.3451 | 1.92286 | 18.90 |
| 12 | −3.1859 | 0.1151 | | |
| 13 | 2.5296 | 0.5493 | 1.755 | 52.32 |
| 14 | 9.7889 | 0.6041 | | |

-continued

Unit mm

| | | | | |
|---|---|---|---|---|
| 15 | ∞ | 0.4483 | 1.51633 | 64.14 |
| 16 | ∞ | 0.4025 | 1.5051 | 63.26 |
| 17 (Image plane) | ∞ | | | |

Aspherical surface data
1st surface k = 0.0000
A4 = 6.1119E−02, A6 = −3.0314E−02, A8 = 2.4111E−02

Various data

| | |
|---|---|
| FNO | 2.5 |
| ω | 40 |
| FL | 0.832 |
| Δ | 0.6631 |

Example 7

Unit mm
Surface data

| Surface no. | r | d | nd | vd |
|---|---|---|---|---|
| 1* | 4.4324 | 0.3126 | 1.80610 | 40.92 |
| 2 | 0.6524 | 0.5442 | | |
| 3 | 1.8152 | 0.5699 | 1.84666 | 23.78 |
| 4 | ∞ | 0.0734 | | |
| 5 | ∞ | 0.3604 | 1.52134 | 65.13 |
| 6 | ∞ | 0.03 | | |
| 7 (Stop) | ∞ | 0.045 | | |
| 8 | −1.3459 | 0.5837 | 1.84666 | 23.78 |
| 9 | −1.2341 | 0.034 | | |
| 10 | 2.9042 | 0.7599 | 1.72916 | 54.68 |
| 11 | −0.8862 | 0.3028 | 1.92286 | 18.90 |
| 12 | −2.4801 | 0.0924 | | |
| 13 | 2.1358 | 0.5495 | 1.755 | 52.32 |
| 14 | 4.6796 | 0.3801 | | |
| 15 | ∞ | 0.4 | 1.51633 | 64.14 |
| 16 | ∞ | 0.5 | 1.5051 | 63.26 |
| 17 (Image plane) | ∞ | | | |

Aspherical surface data
1st surface k = 0.0000
A4 = 8.3469E−02, A6 = −4.441E−02, A8 = 3.9131E−02

Various data

| | |
|---|---|
| FNO | 2.5 |
| ω | 39.9 |
| FL | 0.749 |
| Δ | 0.6107 |

Next, the values of conditional expressions (1) to (5) in each example are shown below.

| Conditional expression | Example 1 | Example 2 | Example 3 | Example 4 |
|---|---|---|---|---|
| (1) $|R1/R2|$ | 0.90 | 0.97 | 0.97 | 1.00 |
| (2) $|R1/F1|$ | 1.40 | 1.76 | 1.74 | 1.84 |
| (3) $\Delta_{ASP}/FL$ | 0.0234 | 0.0274 | 0.0237 | 0.0356 |
| (4) $|Fc/FL|$ | 6.09 | 6.25 | 6.20 | 5.82 |
| (5) $|Fr/Ff|$ | 2.75 | 2.44 | 2.50 | 2.76 |

| Conditional expression | Example 5 | Example 6 | Example 7 |
|---|---|---|---|
| (1) $|R1/R2|$ | 0.73 | 1.04 | 1.09 |
| (2) $|R1/F1|$ | 0.81 | 1.66 | 1.80 |
| (3) $\Delta_{ASP}/FL$ | 0.0127 | 0.014 | 0.0135 |
| (4) $|Fc/FL|$ | 6.61 | 6.0 | 6.11 |
| (5) $|Fr/Ff|$ | 1.70 | 3.76 | 4.83 |

According to the objective optical system for endoscope of the present embodiment, it is possible to provide an objective optical system for endoscope in which, in addition to the distortion, the astigmatism and the curvature of field are corrected favorably.

As described heretofore, the present invention is useful for an objective optical system for endoscope in which, in addition to the distortion, the astigmatism and the curvature of field are corrected favorably.

What is claimed is:

1. An objective optical system for endoscope, comprising in order from an object side:
a first group having a negative refractive power;
an aperture stop; and
a second group having a positive refractive power, wherein
the first group includes in order from the object side, a negative meniscus lens having a convex surface directed toward the object side, and a positive lens having a convex surface directed toward the object side, and
the second group includes in order from the object side, a predetermined lens, a positive cemented lens, and a positive single lens, or includes in order from the object side, the predetermined lens, the positive single lens, and the positive cemented lens, and
the negative meniscus lens has an aspheric surface, and
the predetermined lens is a meniscus lens having a convex surface directed toward an image side, and
the positive cemented lens includes an object-side lens positioned on the object side and an image-side lens positioned on the image side, and
the following conditional expressions (1'), (2), and (4') are satisfied:

$$0.7 < |R1/R2| < 1.1 \quad (1'),$$

$$0.6 < |R1/FL| < 3 \quad (2), \text{ and}$$

$$5 \leq |Fc/FL| \leq 7 \quad (4')$$

where,
R1 denotes a paraxial radius of curvature of a surface on the object side of the predetermined lens,
R2 denotes a paraxial radius of curvature of a surface on an image side of the predetermined lens,
FL denotes a focal length of the overall objective optical system for endoscope,
Fc denotes a focal length at a cemented surface of the positive cemented lens,
here,
the focal length Fc at the cemented surface is expressed by the following expression (b)

$$Fc = Rc/(nd'-nd) \quad (b)$$

Rc denotes a paraxial radius of curvature of the cemented surface, nd denotes a refractive index of the object-side lens for a d-line, and nd' denotes a refractive index of the image-side lens for the d-line.

2. The objective optical system for endoscope according to claim 1, wherein the following conditional expression (3) is satisfied:

$$0.005 \leq \Delta_{ASP}/FL \leq 0.08 \quad (3)$$

where, $\Delta_{ASP}$ denotes an aspheric surface amount at a point of intersection of a principal light ray at the maximum image height and an aspheric surface, FL denotes the focal length of the overall objective optical system for endoscope, and here, the aspheric surface amount $\Delta_{ASP}$ is expressed by the following expression (a)

$$\Delta_{ASP} = \frac{c\rho^2}{1 + \sqrt{1 - (K+1)c^2\rho^2}} + \sum_i A_i \rho^i - \frac{c\rho^2}{1 + \sqrt{1 - c^2\rho^2}} \quad (a)$$

where, c denotes a reciprocal of a paraxial radius of curvature at the aspheric surface, ρ denotes a distance from an optical axis up to the point of intersection, which is a distance in a plane orthogonal to the optical axis including the point of intersection, K denotes a conical coefficient, and $A_i$ denotes an aspherical coefficient.

3. The objective optical system for endoscope according to claim 1, wherein the following conditional expression (5) is satisfied:

$$1.5 \leq |Fr/Ff| \leq 5 \quad (5)$$

where,

Ff denotes a focal length of a negative meniscus lens having the convex surface directed toward the object side, and Fr denotes a focal length of the positive single lens.

* * * * *